(12) United States Patent
Delecluse et al.

(10) Patent No.: US 6,291,246 B1
(45) Date of Patent: Sep. 18, 2001

(54) DNA VIRUS VECTORS AND METHODS FOR THEIR PREPARATION

(75) Inventors: Henri-Jacques Delecluse; Dagmar Pich; Wolfgang Hammerschmidt, all of Munich (DE)

(73) Assignee: GSF Forshungszentrum fur Umwelt und Gesundheit GmbH Ingolstradter, Oberschlesibheim (DE)

(*) Notice: Subject to any disclaimer, the term of this patent is extended or adjusted under 35 U.S.C. 154(b) by 0 days.

(21) Appl. No.: 09/184,987

(22) Filed: Nov. 3, 1998

(30) Foreign Application Priority Data

Nov. 5, 1997 (DE) .............................. 197 48 895
Mar. 27, 1998 (DE) .............................. 198 13 776

(51) Int. Cl.[7] .................................................. C12N 15/74
(52) U.S. Cl. ...................... 435/477; 435/320.1; 435/465; 435/235.1
(58) Field of Search .............................. 435/235.1, 477, 435/465, 320.1

(56) References Cited

U.S. PATENT DOCUMENTS

| 5,194,601 | 3/1993 | Sugden et al. . |
| 5,348,886 | 9/1994 | Lee et al. ........................ 435/320.1 |

FOREIGN PATENT DOCUMENTS

| 19733364 | 2/1999 | (DE) . |
| 694613 | 1/1996 | (EP) . |

OTHER PUBLICATIONS

Delecluse et al., Propagation and recovery of intact, infectious Epstein–Barr virus from prokaryotic to human cells. Proc. Natl. Acad. Sci. USA 95:8425–8520, 1998.

Messerle et al., Cloning and mutagenesis of herpesvirus genome as an infectious bacterial artificial chromosome. Proc. Natl. Acad. Sci. USA 94:14759–14763, 1997.

Shizuya et al., Cloning and Stable maintenance of 300–kilobase–pair fragments of human DNA in *Escherichia coli* using an F–factor–based vector.

Krisky, et al., "Rapid Method for Construction of Recombinant HSV Gene Transfer Vectors", *Gene Therapy* (1997) vol. 4, pp. 1120–1125.

O'Connor et al., "Construction of Large DNA Segements in *Escherichia coli*", *Science*, (1989), vol. 4, p. 1307–1312.

Kempkes et al, "Immortalization of Human Primary B Lmphocytes in vitro with DNA", *Proc. Natl. Acad. Sci.*, USA, Jun. 1995, pp. 5878–5879.

Kempkes et al., "Immortalization of Human B Lymphocytes by a Plasmid Containing 712 Kilobase Pairs of Epstein–Barr Virus DNA", *Journal of Virology*, Jan. 1995, pp. 231–238.

Baer et al., "DNA Sequence and Expression of The B95–8 Epstein–Barr Virus Genome", *Nature*, vol. 310, Jul. 1984, pp. 207–211.

Cherepanov et al., "Gene Disruption in *Escherichia coli*: Tc[R] and Km[R] cassettes with the option of Flp–catalyzed excision of the antibiotic–resistance determinant", *Gene 08901*, 1995, pp. 9–14.

Cohen et al., "Epstein–Barr Virus Nuclear Protein 2 is a Key Determinant of Lymphocyte Transformation", *Proc. Natl. Acad. Sci*, USA, vol. 86, Dec. 1989, pp. 9558–9562.

Hammerschmidt et al., "Identification and Characterization of oriLyt, a Lytic Origin of DNA Repliction of Epstein–Barr Virus", Cell, vol. 55, Nov. 4, 1988, pp. 427–433.

Hammerschmidt et al., "Genetic Analysis of Immortalizing functions of Epstein–Barr Virus in Human B Lymphocytes", *Nature*, vol. 340, Aug. 3, 1989, pp. 393–397.

Hanahan "Studies of Transformation of *Escherichi coli* with Plasmids", *J. Mol. Biol.*, (1983) vol. 166, pp. 557–580.

Yates et al., "Stable Replication of Plasmids Derived From Epstein–Barr Virus in Various Mammalian Cells", *Nature*, vol. 313, Feb. 28, 1985, pp. 812–815.

Firth et al., "Structure and Function of the F Factor and Mechanism of Conjugation", *Escherchia coli and Salmonella*, Second Edition, vol. 2., 1996) pp. 2377–2401.

*Site–specific insertion DNA into a pseudorabies virus vector*, Sauer et al., Proc. Natl. Acad. Sci. USA, vol. 84, pp. 9108–9112, Dec. 1987 Genetics.

*Primary Examiner*—Donna C. Wortman
(74) *Attorney, Agent, or Firm*—Hunton & Williams

(57) ABSTRACT

The invention relates to a method for the preparation of DNA virus vectors capable of replication in eukaryotic as well as in prokaryotic cells as well as to DNA virus vectors prepared by this method. Preferably, the method is used to prepare Epstein-Barr virus vectors.

29 Claims, 5 Drawing Sheets

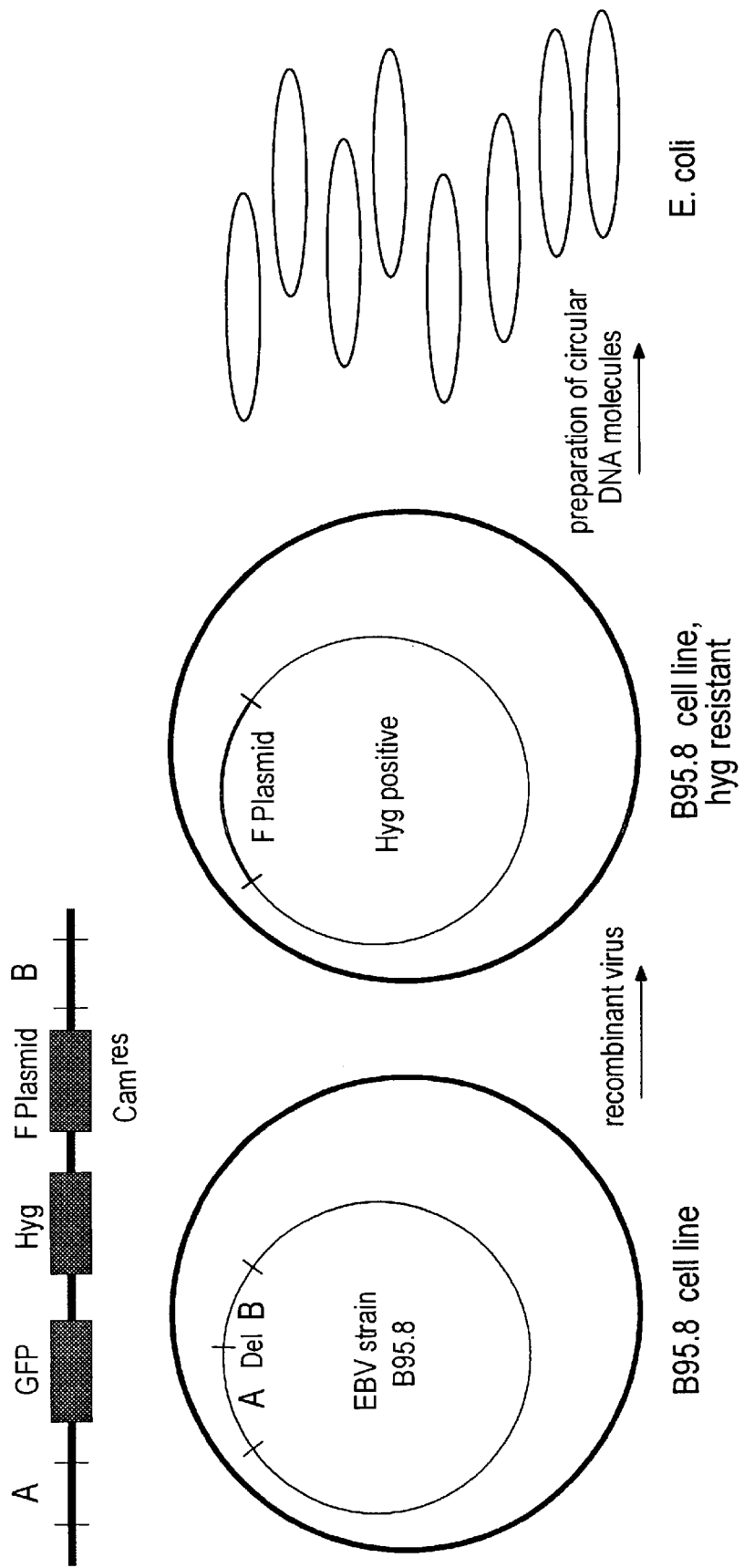
FIG.1: Cloning of genomic B95.8 DNA in E. coli using an F factor plasmid

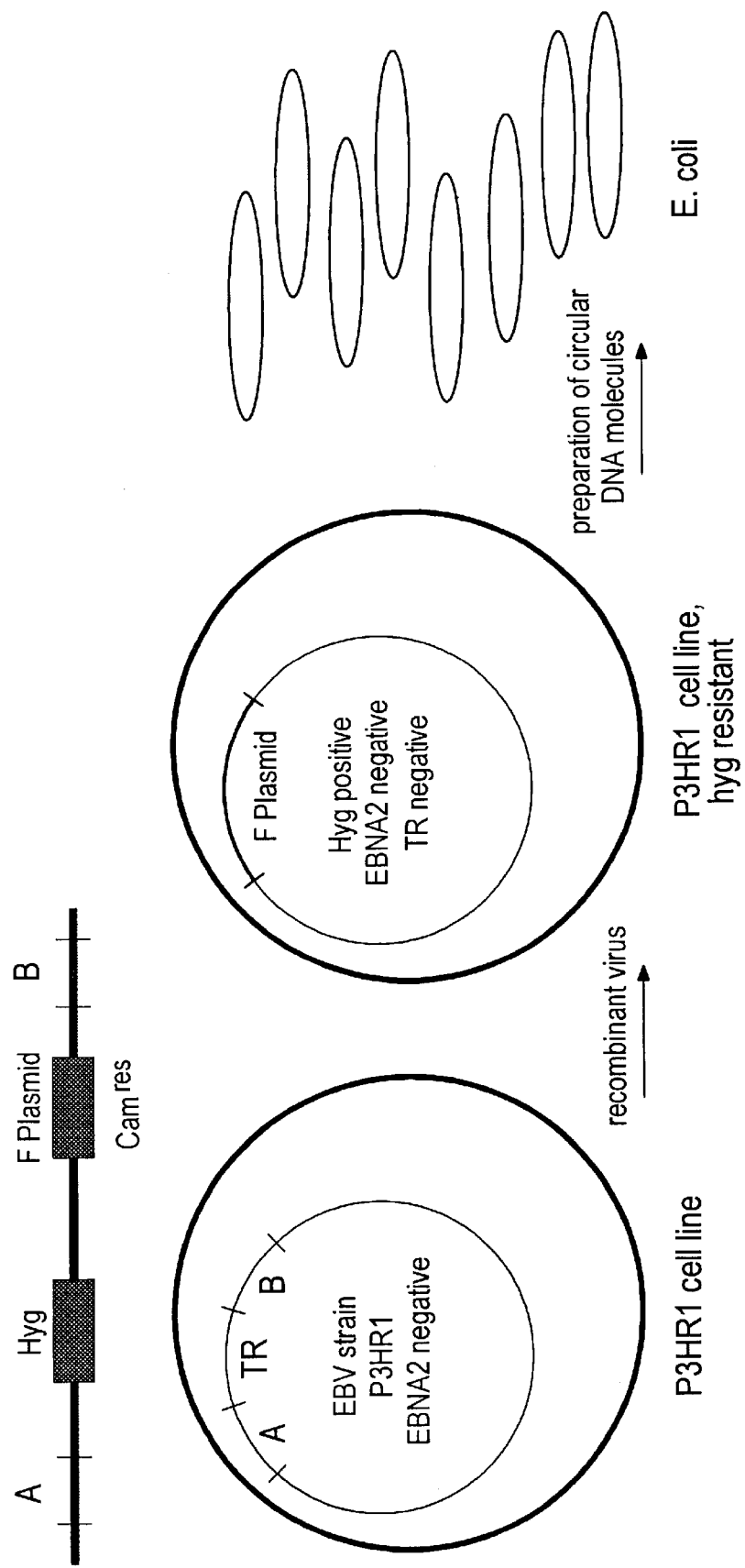
FIG. 2: Cloning of genomic P3HR1 DNA without packaging signals (TR) in E. coli using an F factor plasmid

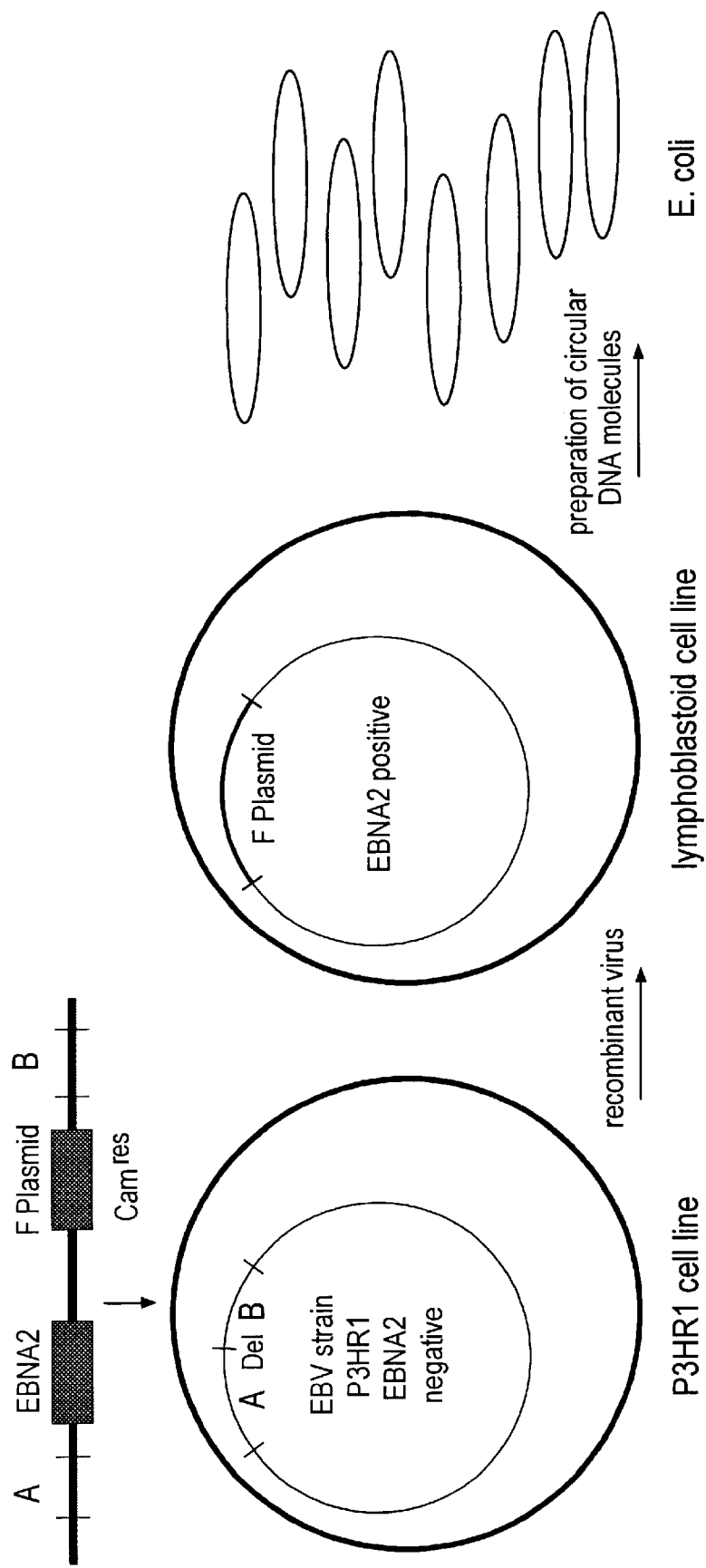
FIG.3: Cloning of genomic P3HR1 DNA in E. coli using an F factor plasmid

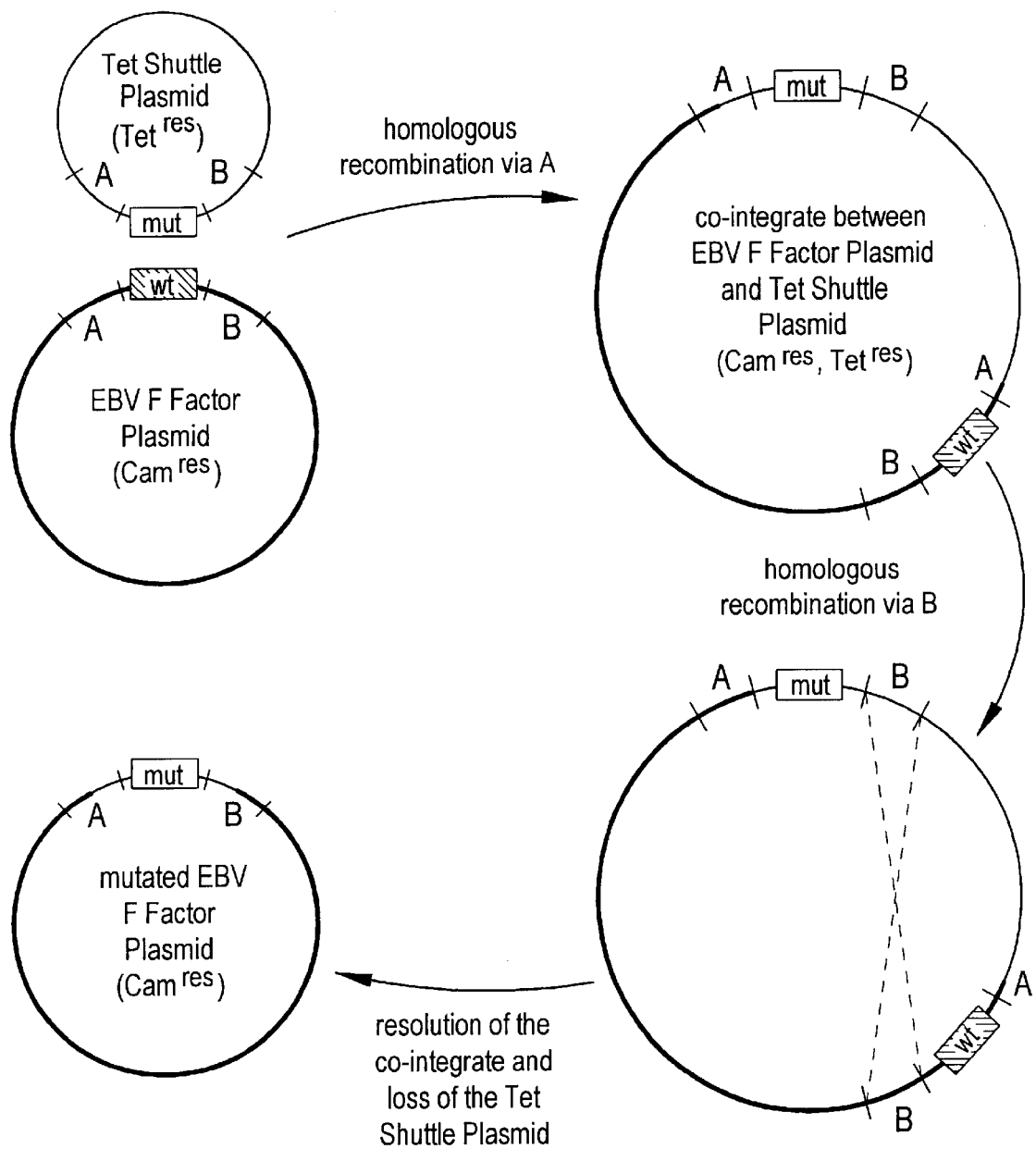
FIG.4: Introduction of mutations in genomic EBV DNA cloned into F factor by allelic exchange

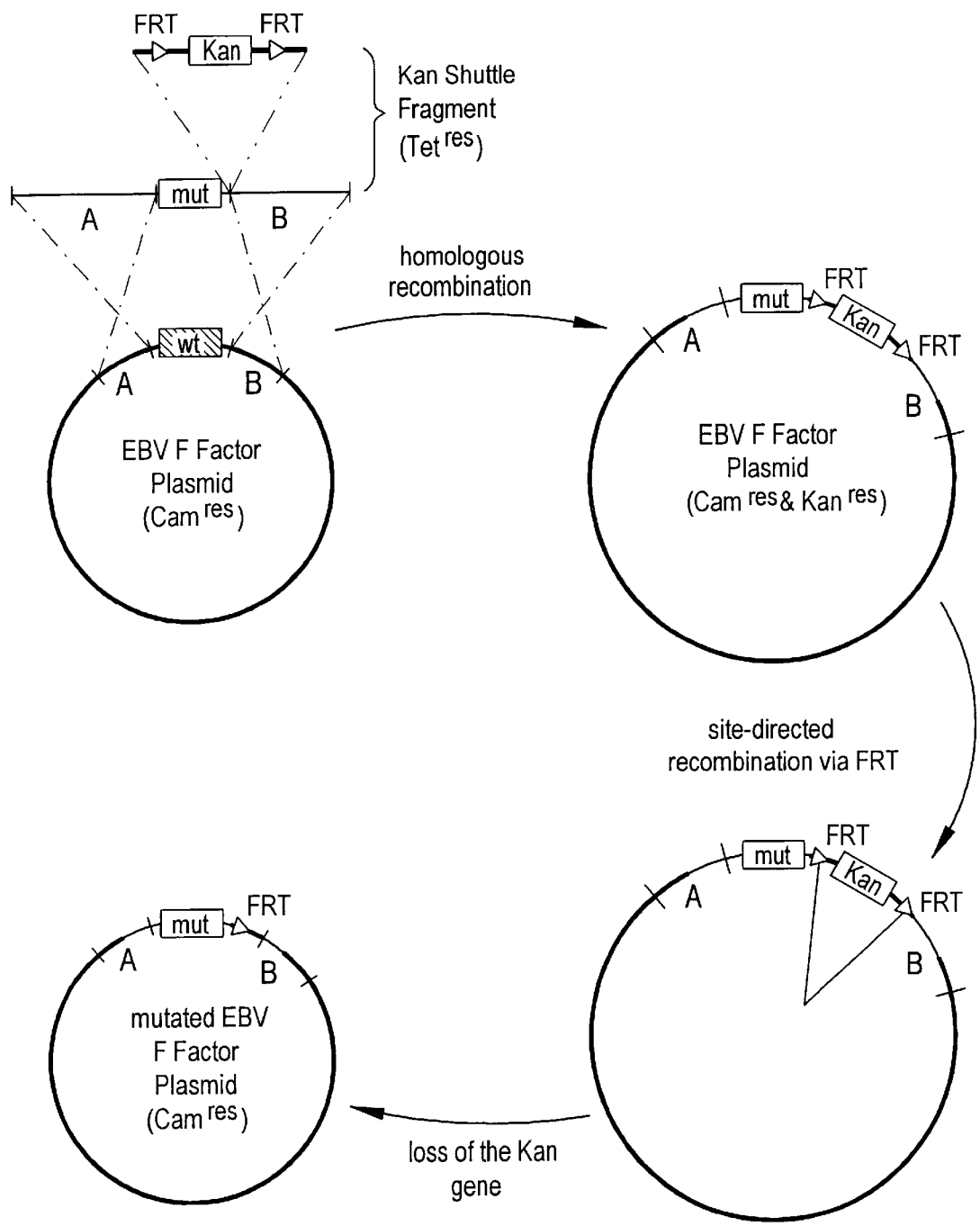
FIG.5: Introduction of mutations into genomic EBV DNA cloned into F factor by selective integration

DNA VIRUS VECTORS AND METHODS FOR THEIR PREPARATION

BACKGROUND OF THE INVENTION (i) Field of the Invention

The present invention relates to a method for the preparation of DNA virus vectors capable of replicating in eukaryotic as well as in prokaryotic cells, and to the DNA virus vectors prepared by said method as well as to cells containing said vectors.

(ii) Description of Related Art

Epstein-Barr virus is one of several herpes viruses in humans. The DNA sequence of the EBV B95.8 isolate has been determined (Baer et al., 1984), and detailed scientific evidence has been worked out mainly with respect to DNA elements which play important roles in the two EBV phases. In the so-called 'latent phase' the virus establishes a stable host cell relation during which the vitality of the cell remains unaffected, however, the viral DNA genome is replicated in the form of an extrachromosomal plasmid in the host cells and passed on into the daughter cells. The latent phase may be associated with a transformation or immortalization, respectively, of the cells infected in a latent manner. The replication origin of the plasmid, oriP, is the DNA element essential for maintenance and replication of the EBV genome in the latent phase. (Yates et al., 1985). This DNA element is also active in recombinant plasmids and has been used as such in several ways.

In the so-called 'lytic or productive phase' the virus is produced in active manner which in addition to the expression of almost all of the viral proteins necessary for regulation of expression or for expression of structural viral components involves two other DNA elements of the virus: the lytic origin of replication, oriLyt, is responsible for viral DNA amplification (Hammerschmidt and Sugden, 1988), the terminal repeats, TR, are packaging signals indispensable for encapsidation of the amplified EBV DNA (Hammerschmidt and Sugden, 1989).

There is a broad interest in the genetic analysis of EBV functions as well as the construction of recombinant EBV genomes. The interest is based on the fact that EBV genomes may bear additional therapeutical genes or that certain undesired properties or genes of EBV may be removed. The techniques used so far in the alteration of the EBV genome are based on homologous recombination events of recombinant *E. coli* plasmids with EBV genomes in cell lines infected by EBV in the latent manner (Cohen et al., 1989; Hammerschmidt and Sugden, 1989). Alternatively, so-called mini EBV genomes may be prepared in *E. coli* which, however, only contain the viral gene functions important for the latent phase of EBV (Sugden and Hammerschmidt, 1993; Hammerschmidt and Sugden, 1995; Kempkes et al., 1995a; Kempkes et al., 1995b).

DISADVANTAGES OF THE RELATED ART

Up to now it has been impossible to alter or to delete any gene of DNA viruses $\geq 100$ kbp, for example of EBV, in a targeted manner and with high efficiency. Thus, homologous recombination events between an EBV segment cloned in *E. coli* and the endogenous EBV present in cell lines infected in a latent manner are inaccurate, difficult to control and must be rendered detectable by means of co-transfected marker segments or selectable genes. In the present prior art, such approaches are not universally applicable, are slow and do not enable the alteration of genes or genomic segments of DNA viruses $\geq 100$ kbp of EBV, such as those necessary for the maintenance of the EBV virus latent phase in the infected cells.

SUMMARY AND OBJECTS OF THE INVENTION

It is an object of the present invention to provide a method for the preparation of DNA virus vectors capable of replication in eukaryotic as well as in prokaryotic cells which enables the preparation of recombinant DNA viruses having a genome $\geq 100$ kbp.

Thus, according to the invention the disadvantages of the prior art have been overcome by cloning the entire DNA virus genome of viruses having a size of $\geq 100$ kbp in the form of a functional unit. A prerequisite of the cloning e.g. in *E. coli* as a recombinant molecule is the ability to integrate a so-called prokaryotic gene segment into the intact DNA virus genome. Integration of this segment containing replicational functions and a selectable marker for *E. coli* ensures that said recombinant molecule of a size of more than 100 kbp may be transfected e.g. into *E. coli* and stably replicated therein. In addition, this event ensures that a modification of any DNA virus segment e.g. in *E. coli* will be possible by means of conventional recombinant DNA technologies.

BRIEF DESCRIPTION OF THE DRAWINGS

FIG. 1: The cloning of genomic B95.8 DNA in *E coli* using a F factor plasmid.

FIG. 2: The cloning of genomic P3HR1 DNA lacking packaging signals (TR) in *E coli* using a F factor plasmid.

FIG. 3: The cloning of genomic P3HR1 DNA in *E coli* using a F factor plasmid.

FIG. 4: The introduction of mutations into the EBV DNA cloned into F factor by allelic exchange.

FIG. 5: The introduction of mutations into the EBV DNA cloned into F factor by selective integration.

DETAILED DESCRIPTION OF PREFERRED EMBODIMENTS

In the following the method of the invention will be explained with respect to a herpes virus, namely EBV, as an example.

The method described permits the preparation of recombinant herpes virus genomes which may be amplified as clones in *E. coli*. With complete certainty it will be possible to adopt this method for all large DNA viruses (such as pox viruses, iridio viruses, other herpes viruses, baculoviruses). Cloning of these viral genomes e.g. in *E. coli* will enable the simple modification by site-directed alteration of viral genes, the deletion thereof or the addition of further genes of interest. The resulting viral genomes will have novel properties depending on the genetic modification which enable for example the expression of foreign proteins in the corresponding target cells of the viruses.

The viral genomes cloned for example in *E. coli* present a product useful for the preparation of viral particles such as those suitable for encapsidation of recombinant plasmids or subgenomic viral segments.

The method according to the invention is useful in the preparation of DNA virus vectors capable of replication in eukaryotic as well as prokaryotic cells and comprises at least the following steps of:

a) Introducing a DNA virus genome $\geq 100$ kbp into an eukaryotic target cell and establishing such cells containing the viral DNA genome at least in extrachromosomal form;

b) introducing a DNA segment into the eukaryotic target cell at least comprising, operably linked to each other, the information for replication of the viral DNA genome in prokaryotic cells and at least one marker gene selectable in prokaryotic cells, and which is flanked by DNA segments (homologous segments) of the DNA virus genome having a length which enables recombination;

c) integrating the segments defined in (b) into the DNA virus genome by recombination; optionally d) selecting such target cells containing an extrachromosomal recombinant viral DNA genome; and optionally e) purifying and isolating the recombinant DNA virus vector genome.

The method of the invention is different from methods known to date for the preparation of DNA virus vectors particularly in that for the first time the preparation of such vectors from DNA viruses having a size of $\geq 100$ kbp becomes possible. For example, by the method used up to now DNA viruses such as adenoviruses having a size of about 40 kbp were cloned. The preparation of DNA virus vectors having a size of $\geq 100$ kbp, particularly $\geq 120$ kbp, and preferably $\geq 150$ kbp or especially preferred $\geq 170$ kbp was impossible with the methods known from the prior art.

The method according to the invention is not only useful for the preparation of recombinant herpes virus genomes reproducible in prokaryotic cells as well as in eukaryotic cells but also e.g. for the preparation of recombinant pox virus or iridio virus or baculovirus genomes.

The herpes virus may be an alpha herpes virus, a beta herpes virus, or a gamma herpes virus. Examples of those viruses are: alpha herpes virus: herpes simplex virus (HSV), varicella zoster virus (VZV); beta herpes virus: cytomegalovirus (CMV); gamma herpes virus: Epstein-Barr virus (EBV).

Introduction of the DNA virus into the eukaryotic target cell may be effected by methods known per se; examples of such methods are infection, transfection, or electroporation. The same applies to the introduction of the DNA segment into the eukaryotic target cell in step (b).

As an alternative to the process step (a) in which the DNA virus is introduced into the eukaryotic target cell such cells may be used which already contain the DNA virus in an extrachromosomal form.

A target cell according to the invention is meant to be any cell having virus receptors and in which the virus is able to replicate.

Furthermore, besides the DNA virus also a DNA segment is introduced into the eukaryotic target cell comprising at least the information for replication of the viral genome in prokaryotic cells and a marker gene which may be selected for in prokaryotic cells. These gene segments are flanked by DNA segments having a length which enables recombination with the DNA virus. The flanking DNA segments have homologies to the DNA virus enabling a recombination, and particularly a homologous recombination. The length of the flanking DNA sequences preferably is $\geq 300$ bp, further preferred $\geq 1$ kbp and especially preferred $\geq 2$ kbp.

Preferably, integration of the segments described in step (b) into the DNA virus genome is carried out by homologous recombination in the DNA virus target cell. However, it is also possible that an illegitimate recombination will lead to the desired result. Normally, however, a homologous recombination will permit to achieve the recombining DNA virus genome.

The DNA segment in step (b) may be linearized prior to introduction into the eukaryotic target cell. In this manner, the ends will be protected against degradation by endogenous nucleases.

In a preferred embodiment of the invention the information for replication of the viral DNA genome will be localized in prokaryotes and the information for the marker gene selectable in prokaryotic cells will be on the *E. coli* F plasmid. In another preferred embodiment of the invention the DNA segment in step (b) will additionally contain at least one marker gene selectable in eukaryotic cells. As selectable markers any markers selectable in prokaryotic cells or in eukaryotic cells, respectively, may be used. Examples for such markers are in particular antibiotic resistance genes and fluorescence marker genes.

F factor-derived plasmids of about 5 kbp generally contain the following segments and genes of the *E. coli* F factor plasmid which in its naturally occuring form encompasses about 100 kbp: for maintaining the copy number of about 1 to 2 copies/*E. coli* cell the genes parA and parB are essential, oriS and the gene repE are necessary for DNA replication. All those elements are present on the F factor plasmid used for example for the generation of the EBV/F factor construct.

In a further embodiment of the invention the DNA segment in process step (b) contains at least one gene of interest encoding for example a protein of the blood coagulation cascade, e.g. the factor VIII gene. Any gene known per se may be localized on the DNA segment and may be introduced by the method of the invention into the DNA virus shuttle vector. In this manner it will be possible to express the gene of interest in an eukaryotic cell or in a prokaryotic cell.

The method of the invention enables the cloning of complete DNA virus genomes having a size of $\geq 100$ kbp. An especially preferred example is the EBV genome having a size of about 170 kbp.

In an embodiment of the present invention the homologous regions in (b) are selected in a manner to introduce a mutation into the viral genome. A mutation according to the invention is meant to be a point mutation, a mutation affecting several nucleotides, a deletion, an addition, or an exchange of nucleotides. The addition of nucleotides also comprises the introduction of one or more genes encoding for example a gene of interest, mainly a gene of therapeutical value.

In an embodiment of the method according to the invention the flanking regions in process step (b) are selected to delete the terminal repeats in the herpes virus genome. Following recombination with the DNA virus genome a packaging-deficient viral genome will be generated so that following induction of the lytic phase of EBV in the target cells no infectious particles will be released while simultaneously, however, all of the viral proteins and functions for the packaging of DNA molecules will be available in trans.

In another embodiment of the invention the recombinant DNA virus vector genome obtained according to the invention will be mutated in further process steps. A definition of the understanding of 'mutation' has been already given above. The introduction of mutations may be effected either in the way described above or by introducing the resulting DNA virus vector genome into a prokaryotic cell or into another eukaryotic cell and by introducing the mutations in those cells, for example by further recombination events. In a preferred embodiment of the invention a mutation is introduced in one or more of the cis-acting segments of the viral DNA genome where the mutation alters the packaging of the viral DNA genome.

In an embodiment of the invention which is particularly preferred according to the invention the prokaryotic portions of the DNA segment in step (b) will be selected to contain sequences with at least partial homology to each other having a length that enables homologous recombination whereby the prokaryotic portions of the DNA segment of (b) are eliminated. By such a homologous recombination the prokaryotic portions introduced by the method according to the invention are eliminated in subsequent process steps. In this manner, for example antibiotic resistances introduced by introduction of the DNA segment into the eukaryotic target cell and other prokaryotic portions may be removed yielding a DNA virus vector useful in gene therapy in which the proportion of prokaryotic foreign sequences is as low as possible. An example for this will be described in more detail in the Examples.

Furthermore, according to the invention a DNA virus vector is provided comprising at least a DNA virus genome $\geq 100$ kbp, at least a marker gene selectable in prokaryotic cells and the information for replication of the viral DNA genome in prokaryotic cells, operably linked to each other.

In the following, the invention will be described with respect to the Figures and the Examples below. The Examples represent preferred embodiments of the invention. However, the invention is not limited to these specific Examples.

Into two different cell lines infected with two different EBV strains in a latent manner (B95.8 and P3HR1/HH514) a segment of the E. coli plasmid F factor was introduced comprising the functions for replication and a marker selectable in E. coli. This linear region of the F factor plasmid was flanked on the right and on the left each by EBV regions so that the F factor segment could be targeted into the endogenous EBV genome in the cell lines via two homologous recombination events. In addition to the flanking EBV regions the DNA fragment contains at least a marker gene suitable for selection (e.g. hygromycin phosphotransferase) or phenotypic characterization (e.g. green fluorescence protein, GFP) in eukaryotic cells. This construct is transfected into EBV-infected cells where homologous recombination with the endogenous EBV genome and the site-directed integration of the F factor segment together with the marker gene occur. Afterwards, the cell lines thus modified harbour a recombinant EBV genome which may be transferred into E. coli in a shuttle system. The recombinant EBV genome will replicate in E. coli via its F factor portion also carrying the prokaryotic selection marker. Other genetic alterations of the recombinant EBV genome may be effected using conventional genetic techniques in E. coli.

The recombinant EBV genome may be isolated from E. coli and the DNA molecules may be prepared using conventional techniques. These DNA molecules are then introduced by DNA transfer techniques stably or transiently into eukaryotic cells. The recombinant EBV genomes will replicate extrachromosomally in these cells such as in the cell lines B95.8 and P3HR1/HH514 infected in a latent manner. Spontaneously or following chemical induction or induction effected by other means of the lytic phase of EBV the synthesis of recombinant Epstein-Barr virions will occur which are released into the cell culture supernatant and are available for other uses.

Methods of Preparation

Using the method described above, a F factor segment was introduced into the B95.8 virus genome containing the eukaryotic selection marker hygromycin phosphotransferase and the phenotypic marker gene GFP in addition to functional F factor components. The recombinant B95.8 genome was generated, transferred into E. coli, and recombinant EBV DNA was prepared from E. coli. This DNA was introduced into several EBV-negative cells (293, EBV-negative Akata, neuronal cells). Induction of the lytic cycle resulted in the release of infectious virions containing recombinant EBV genome as the genetic information. These recombinant EBV genomes are able to e.g. immortalize primary human B lymphocytes.

In two independent experiments two different segments of the F factor were introduced into the P3HR1/HH514 virus genome into two different genomic sites. Targeting for these genomic sites was performed using different EBV flanking regions. In one experiment another EBV gene was introduced, in the second experiment a targeted deletion of an EBV region was performed by selecting the EBV flanking regions.

The recombinant B95.8 as well as P3HR1/HH514 viral genomes were further modified in E. coli by deletions or introduction of new genes.

EXAMPLES

1. Cloning of a Fully Functional Genome of the B95.8 Strain

An F factor plasmid referred to as p1944.12 (Table 1) was generated in E. coli using conventional DNA cloning techniques. As shown schematically in FIG. 1 the plasmid contains two regions A and B representing the subgenomic regions of the B95.8 genome. The nucleotide sequence coordinates of these segments are reported in Table 1. The regions A and B flank the pMBO131 replicon (O'Connor et al., 1989) comprising the prokaryotic origin of replication of the F factor together with the selectable prokaryotic marker gene chloramphenicol acetyl transferase (cam). Furthermore, the eukaryotic marker gene hygromycin phosphotransferase (Hyg) expressed by the SV40 early promoter/enhancer and the marker gene green fluorescence protein (GFP) of the immediate early promoter/enhancer of human cytomegalovirus are contained in plasmid p1944.12 (Table 1 and FIG. 1). Portions of the p1944.12 plasmid important for function are the EBV segments, the pMBO131 portion and the Hyg, GFP genes are optional.

The regions A and B of the B95.8 genome on p1944.12 are selected to flank the natural deletion in the genome of B95.8 on the left and on the right. To introduce this plasmid into the B95.8 genome it was linearized with NotI restriction enzyme, and the free DNA ends were sealed by so-called hairpin oligonucleotides using T4 DNA ligase to protect them against exonucleases. The plasmid DNA thus modified was transfected into the B95.8 cells by electroporation and the cells were selected in the presence of 100 µg/ml of hygromycin. Under these selection conditions only cells survive which have taken up and integrated p1944.12 DNA either into the host cell genome or into the extrachromosomal genomic copies of the B95.8 EBV strain. To distinguish between those two possibilities single cell clones were investigated by Gardella agarose gels and subsequent Southern blot hybridization. By these analytical techniques it was possible to identify a number of cellular clones which had integrated p1944.12 into the genomic copies of the B95.8 EBV strain.

For the cloning of these genetically altered EBV genomes in E. coli the plasmid DNA was isolated from the cellular clones, transferred into E. coli strain DH10B using electroporation techniques and selected by means of chloramphenicol resistance. Subsequent isolation of plasmid DNA from E. coli resulted in DNA preparations which following digestion with several restriction enzymes showed DNA fragments corresponding exactly to the composition of B98.8 DNA including the integrated p1944.12 portion. The total size of these EBV genomes was more than 170 kbp and has been referred to as 2010.

2010 DNA was isolated in the microgram scale from *E. coli* and introduced into EBV-negative eukaryotic cells via several DNA transfection methods. These cells may be for example EBV negative Akata cells, 293 cells and fibroblast cells or cell lines. These cells were selected under adjusted hygromycin concentrations to ensure the stable introduction of 2010 DNA into the cells. The EBV lytic phase was induced by several techniques, such as by transfection of the BZLF1 expression plasmid pCMV-BZLF1(Hammerschmidt and Sugden, 1988). Induction of the EBV lytic phase in these cells results in the release of infectious viruses capable of immortalizing primary human B lymphocytes. To detect this property of 2010 EBV a cell-free supernatant from lytically induced cells was obtained and used to infect primary human B lymphocytes. Four to six weeks after infection of these cells it was possible to establish permanently proliferating cell lines containing 2010 EBV DNA as was proven via different techniques (Southern blot hybridization, PCR analysis).

2. Cloning of a Packaging-Deficient P3HR1/HH514 genome in *E. coli*

An F factor plasmid referred to as p2061.2 (Table 1) was generated in *E. coli* using conventional DNA cloning techniques. As shown schematically in FIG. 2 the plasmid contains two regions A and B representing the subgenomic regions of the P3HR1/HH514 genome. The nucleotide sequence coordinates of these segments are reported in Table 1. The regions A and B flank the pMBO131 replicon (O'Connor et al., 1989) comprising the prokaryotic origin of replication of the F factor together with the selectable prokaryotic marker gene chloramphenicol acetyl transferase (cam). Furthermore, the eukaryotic marker gene hygromycin phosphotransferase (Hyg) expressed by the SV40 early promoter/enhancer is contained in plasmid p2061.2 (Table 1 and FIG. 2). Portions of the p2061.2 plasmid important for function are the EBV segments, the pMBO131/F factor portion and the Hyg gene.

The regions A and B of the P3HR1/HH514 genome on p2061.2 are selected to flank the 'terminal repeats' in the genome of P3HR1/HH514 on the left and on the right. The 'terminal repeats' (TR) are i.a. characterized by bearing signal sequences necessary for the packaging of viral genomic DNA into EBV capsids. The purpose of the construction of p2061.2 is to delete the TR signal sequences and to replace them by the pMBO131 and Hyg portions of p2061.2. To introduce p2061.2 into the P3HR1/HH514 genome it was linearized with SacI restriction enzyme, and the free DNA ends were sealed by so-called hairpin oligonucleotides using T4 DNA ligase to protect them against exonucleases. The plasmid DNA thus modified was transfected into the P3HR1/HH514 cells by electroporation and the cells were selected in the presence of 200 µg/ml of hygromycin. Under these selection conditions only cells survive which have taken up and integrated p2061.2 DNA either into the host cell genome or into the extrachromosomal genomic copies of the P3HR1/HH514 EBV strain. To distinguish between those two possibilities single cell clones were investigated by Gardella agarose gels and subsequent Southern blot hybridization. By these analytical techniques it was possible to identify a number of cellular clones which had integrated p2061.2 into the genomic copies of the P3HR1/HH514 EBV strain.

For the cloning of these genetically altered EBV genomes in *E. coli* the plasmid DNA was isolated from the cellular clones, transferred into *E. coli* strain DH10B using electroporation techniques and selected by means of chloramphenicol resistance. Subsequent isolation of plasmid DNA from *E. coli* resulted in DNA preparations which following digestion with several restriction enzymes showed DNA fragments corresponding exactly to the composition of P3HR1/HH514 genomic DNA without TR signal sequences but including the integrated p2061.2 portion. The total size of these EBV genomes was more than 170 kbp and has been referred to as 2087.2a.

2087.2a DNA was isolated in the microgram scale and introduced into EBV-negative eukaryotic cells via several DNA transfection methods. These cells may be for example EBV negative Akata cells, 293 cells and fibroblast cells or cell lines. These cells were selected under adjusted hygromycin concentrations to ensure the stable introduction of 2087.2a DNA into the cells. The EBV lytic phase was induced by several techniques, such as by transfection of the BZLF1 expression plasmid pCMV-BZLF1 (Hammerschmidt and Sugden, 1988). In contrast to the Example described in 1. The induction of the EBV lytic phase in these cells does not result in the release of infectious viruses since no packaging of EBV genomic DNA occurs due to the absence of TR packaging signals. However, these cell lines provide all viral functions for the packaging of DNA molecules in trans such as those necessary for the encapsidation of p554 (Hammerschmidt and Sugden, 1989) or of mini EBV plasmids (Kempkes et al., 1995a; Kempkes et al., 1995b) without releasing so-called helper virus (Hammerschmidt and Sugden, 1989).

3. Cloning of a P3HR1/HH514 Genome with Genetic Complementation in *E. coli*

An F factor plasmid referred to as p1820.15 (Table 1) was generated in *E. coli* using conventional DNA cloning techniques. As shown schematically in FIG. 3 the plasmid contains two regions A and B representing subgenomic regions of the B95.8 genome. The nucleotide sequence coordinates of these segments are reported in Table 1. The regions A and B flank the pMBO131 replicon (O'Connor et al., 1989) comprising the prokaryotic origin of replication of the F factor together with the selectable prokaryotic marker gene chloramphenicol acetyl transferase (cam). Furthermore, as functional regions the EBV gene EBNA2 and two exons of the EBV gene EBNA-LP are contained in the p1820.15 plasmid (Hammerschmidt and Sugden, 1989) (Table 1 and FIG. 3). Portions of the p1820.15 plasmid important for function are the flanking EBV segments, the gene EBNA2 and the EBNA-LP gene portions as well as the pMBO131 portion.

The regions A and B of the B95.8 genome on p1820.15 are selected to flank the deletion comprising two EBNA-LP exons and the entire EBNA2 gene in the genome of P3HR1/HH514 on the left and on the right. To introduce this plasmid into the P3HR1/HH514 genome it was linearized with NheI restriction enzyme, and the free DNA ends were sealed by so-called hairpin oligonucleotides using T4 DNA ligase to protect them against exonucleases. The plasmid DNA thus modified was transfected by electroporation into the P3HR1/HH514 cells together with the expression plasmid pCMV-BZLF1 which induces the EBV lytic cycle in these cells. Cell-free culture supernatant was obtained and used to infect primary human B lymphocytes. Four to six weeks following the infection of these cells permanently proliferating cell lines could be established. The deletion in P3HR1/HH514 comprising the entire EBNA2 gene and two exons of the EBNA-LP gene abolishes B cell immortalization. The regions on plasmid p1820.15 complement the deletion in the P3HR1/HH514 virus genome by homologous recombination between P3HR1/HH514 DNA and p1820.15 DNA similar to that described (Hammerschmidt and Sugden, 1989). The EBV genomes after homologous recombination are characterized by their restored ability to immortalize primary human B lymphocytes. At the same time the integration of the F factor portion of p1820.15 occurs making the pMBO131 replicon a component of the recombinant EBV genome. For the cloning of these genetically altered EBV genomes in E. coli the plasmid DNA was isolated from the cellular clones, transferred into E. coli strain DH10B using electroporation techniques and selected by means of chloramphenicol resistance. Subsequent isolation of plasmid DNA from E. coli resulted in DNA preparations which following digestion with several restriction enzymes showed DNA fragments corresponding exactly to the composition of P3HR1/HH514 genomic DNA including the integrated p1820.15 portion. The total size of these EBV genomes was more than 170 kbp and has been referred to as 1947 (K clone).

4. Introduction of Mutations Into Genomic EBV DNA Cloned Into F Factor by Allelic Exchange The cloning of genomic EBV DNA in E. coli permits the simple genetic modification by means of methods which are established or adapted, respectively, for the specific conditions according to the invention.

To exchange the packaging signals in the cloned EBV genome 1947 (Table 1) the recombinant plasmid p2060.1was generated in E. coli which consists of the following components (see FIG. 4):

1. A prokaryotic vector plasmid having a temperature-sensitive origin of replication (Tet shuttle plasmid) and the prokaryotic selection marker tetracycline resistance e.g. on the basis of pMBO96 (O'Connor et al., 1989).

2. Flanking regions A and B containing the EBV sequences of strain P3HR1/HH514 from nucleotide position #165,840 to #169,924 (A) and #1 to #3955 (B).

3. The eukaryotic selection marker hygromycin phosphotransferase expressed by the SV40 early promoter/enhancer. This gene is located between the EBV portions A and B and is indicated by 'mut' in FIG. 4.

The F factor plasmid 1947 (Table 1) is transfected into a recombination competent (recA+) E. coli strain, and the transfectants are identified by means of their chloramphenicol resistance. In a second step the Tet shuttle plasmid p2060.1 is transfected into the transfectants harbouring 1947 and the bacteria are selected at 30° C. for their double resistance against chloramphenicol and tetracycline. Both plasmids replicate independently of each other in the same E. coli cell. The homologous recombination via A (may also be effected via B) is forced by raising the temperature to 42° C. and selecting for resistance against chloramphicol and tetracycline, since the Tet shuttle plasmid p2060.1 is unable to replicate at this temperature. A co-integrate as shown in FIG. 4 is generated. By another homologous recombination, this time via B, the co-integrate is resolved and the Tet shuttle plasmid is lost so that the modification 'mut' (in this case the hygromycin phosphotransferase gene) replaces the EBV sequence 'wt' (in this case the packaging signals TR). The last step takes place according to statistical distribution, i.e. during resolution of the co-integrate either the mutation 'mut' may be introduced (as shown in FIG. 4) or the starting situation 'wt' may be restored.

The advantage of this method in contrast to that described under 5. is the possibility to exchange even single nucleotides in the cloned EBV genome in a targeted manner without needing to introduce other foreign sequences.

5. Introduction of Mutations in Genomic EBV DNA Cloned Into F Factor by Selective Integration A second alternative method for genetic modification of genomic EBV DNA cloned into F factor is the integration of linear DNA fragments by homologous recombination, as shown schematically in FIG. 5.

To mutate the EBV gene LMP2A, a Kan shuttle fragment was first cloned into a common pBR-derived plasmid, as shown in FIG. 5. The Kan shuttle fragment in plasmid p2120 contains two EBV segments A and B containing the EBV sequences of strain B95.8 from nucleotide positions #163,473 to #166,180 (A) and #166,938 to #172,281/#1 to #649 (B). The mutation 'mut' indicated in FIG. 5 consists of two so-called loxP sequence motifs flanking an exon of the LMP2A EBV gene (EBV nucleotide positions #166,181 to #166,937). Contiguous with one of the two loxP sequence motifs there was cloned a selection marker for resistance against the antibiotic kanamycin bounded by FRT sequence motifs. The fragment as shown on the upper left in FIG. 5 is separated from the pBR portion by restriction enzymes and the linear Kan shuttle fragment DNA is isolated. Co-transfection of this linear DNA fragment together with the EBV genome 2010 cloned into F factor is performed into an E. coli strain which preferably is exonuclease V-negative; e.g. the E. coli strain BJ5183 (Hanahan, 1983). Selection of the transfected bacteria for resistance against chloramphenicol and kanamycin forces the homologous recombination between both of the DNA molecules and in the ideal case results in the EBV F factor plasmid shown on the upper right. The kanamycin resistance gene may be removed by site-directed recombination via FRT by FLP recombinase in E. coli. (Cherepanov and Wackernagel, 1995). As the result a mutated EBV F factor plasmid is generated. The basic difference as compared to the situation shown under 4. is the remaining of foreign sequences, namely of a FRT sequence motif.

Antibiotic resistance markers and sequences employed for site-directed recombination may be chosen as desired. This applies similarly also to the approach described in 4.

Moreover, the establishment of a genetic library is considered which may be prepared by transposon-mediated mutagenesis in E. coli and thus represents any large number of individually mutated EBV genomes. By random insertion of the transposon into the cloned EBV genomes a mutagenesis is generated at the site of insertion e.g. a disruption of the reading frame of the EBV gene. The advantage of an EBV genomic library of this type would be the possibility to biologically select for certain phenotypes. A genomic library containing mutated herpes virus genomes may be for example used as a screening system for antiviral substances.

Thus, the method according to the invention may be further modified as follows:

(f) Introduction of a recombinant DNA virus vector genome into a prokaryotic cell;

(g) introduction of a plasmid into the prokaryotic cell containing at least a DNA sequence which bears a mutation compared to the homologous sequence present on the DNA virus vector genome, and a selectable marker gene flanked by DNA segments of a length sufficient to enable a recombination with the DNA virus vector genome, operably linked to each other;

(h) integration of the segment described in (g) by recombination into the DNA virus genome;

(i) optionally purification and isolation of the recombinant DNA vector.

In a further embodiment the plasmid in step (g) further contains sequence motifs which can be recognized by a recombinase; and prior to step (e) the resistance gene introduced by recombination is removed by site-directed recombination via the sequence motifs recognized by the recombinase.

Removal of the prokaryotic replicon and of other foreign portions from the herpes virus genomes cloned in E. coli. Using the gene vectors it is desirable to keep the portion of genetic information introduced into the target cell as small as possible and to restrict it to essential features. In particular, subgenomic segments are undesirable which harbour prokaryotic marker genes such as antibiotic resistances or otherwise represent a potential safety hazard because they may be the reason for homologous recombinations with several bacteria. The EBV genomes cloned using the F factor replicon are such a hybrid molecule. The F factor portion is essential for the propagation of the DNA molecule in E. coli but is completely non-functional in the eukaryotic cell into which the EBV/F factor replicon modified in E. coli is then introduced to prepare genetically modified EBV.

Surprisingly, a convenient method for the complete removal of this F factor portion without further genetic manipulation has been discovered.

In the cloning of a fully functional genome of strain B95.8 in E. coli a F factor plasmid has been used named p1944.12 (Table 1). This was prepared in E. coli using conventional DNA cloning techniques. As shown schematically in FIG. 1, the plasmid consists of two segments A and B representing subgenomic regions of the B95.8 genome. The nucleotide sequence coordinates of these regions are presented in the Table 1; they extend from EBV coordinate #143,458 to #152,636 in region A and from #149,930 to #159,880 in region B. The regions A and B flank the pMBO131 replicon (O'Connor et al., 1989) comprising the prokaryotic origin of replication of the F factor together with the selectable prokaryotic marker gene chloramphenicol acetyl transferase (cam) and other genes. Both of the EBV portions are selected to contain in part the same DNA sequence regions, in the actual example a partial duplication of 2.7 kbp (from #149,930 to #152,636). The F factor plasmid cloned from these experiments in E. coli was named 2010 (Table 1). Following transfection of the 2010 DNA into 293 cells homologous recombination events occur spontaneously between the duplicated portions in the regions A and B in these cells leading to the deletion of all sequences derived from the prokaryotic cloning steps.

At this point, examples are presented with respect to further uses considered:

Establishment of specifically modified DNA viruses lacking particular virulent genes and which may be used as specifically attenuated vaccine strains. In the case of EBV possible virulent genes may be for example EBNA2, LMP1, LMP2A and so on which may be deleted for the purpose of attenuation of the vaccine strain.

Generation of recombinant EBV vectors which in packaging cell lines are provided with an EBV capsid and may be used in gene transfer into human cells or cells of other mammals in vitro or in vivo. These packaging cell lines stably contain an EBV genome or the essential parts thereof necessary for the production of viral structural proteins to package the EBV vectors. The packaging cell lines are preferably provided with an EBV genome lacking its own packaging signals (see FIG. 2 and embodiments) to prevent the release of undesired so-called helper viruses. The EBV vectors which may be packaged may be based on conventional recombinant DNA plasmids containing all of the elements necessary for amplification of their DNA (oriLyt), their packaging (TR), and the stable extrachromosomal existence in the recipient cell (oriP and EBNA1). In addition, these vectors may bear genes of therapeutical interest e.g. factor VIII in the sense of a genetic correction.

Moreover the affinity of such vectors for certain target cells may be altered. EBV glycoproteins responsible for the infection of specific cells (normally B cells and some epithelial cells) may be altered by mutation of the EBV genomes cloned into F factor in E. coli or replaced by others. An example for an extended cell tropism may be the vesicular stomatitis virus glycoprotein G, an example for an extremely specific cell tropism for almost exclusively pluripotent hematopoietic stem cells would be the ligand for stem cell factor receptor on the stem cell, the membrane-bound stem cell factor ligand (mSCF ligand). This so-called pseudo-typing is particularly attractive for herpes virus vectors since the glycoproteins important for infectiousness are embedded into a phospholipid membrane derived from a nuclear membrane. This membrane is essentially unstructured and only loosely encapsulates the strictly geometrical capsid of the virion. In contrast to many smaller viruses (e.g. adeno viruses, adeno-associated virus (AAV), retroviruses) the capsid of herpes viruses and other large DNA viruses is flexible and requires no specific protein configuration or folded structures which otherwise would prevent virus maturation and assembly.

Advantages Over the Prior Art

The method described permits for example the preparation of recombinant herpes virus genomes which may be clonally amplified for example in E. coli. It may be expected with certainty that this method is applicable to all large DNA viruses (e.g. pox viruses, iridio viruses, other herpes viruses). Cloning of these viral genomes e.g. in E. coli allows the simple modification by targeted alterations of viral genes, their deletion or the addition of further genes of interest. The viral genomes prepared in this manner show novel properties depending on the genetic modification such as permitting the expression of proteins in the respective target cells of the viruses.

The viral genomes cloned in E. coli provide a product useful for example for encapsidation of recombinant plasmids or subgenomic viral regions.

REFERENCES

Baer, R., Bankier, A. T., Biggin, M. D., Deininger, P. L., Farrell, P. J., Gibson. T. J., Hatfull. G., Hudson, G. S., Satchwell, S. C., Seguin, C., Tufnell, P. S. und Barell, B. G. (1984) DNA sequence and expression of the B95-8 Epstein-Barr virus genome. Nature (London), 310, 207–211.

Cherepanov, P. P. und Wackemagel, W. (1995) Gene disruption in Escherichia coli: TcR and KmR cassettes with the option of Flp-catalyzed excision of the antibiotic-resistance determinant. Gene, 158, 9–14.

Cohen, J. I., Wang, F., Mannick, J. und Kieff, E. (1989) Epstein-Barr virus nuclear protein 2 is a key determinant of lymphocyte transformation. Proc. Natl. Acad. Sci. U S A, 86, 9558–9562.

Hammerschmidt, W. und Sugden, B. (1988) Identification and characterization of oriLyt, a lytic origin of DNA replication of Epstein-Barr virus. *Cell,* 55, 427–433.

Hammerschmidt, W. und Sugden, B. (1989) Genetic analysis of immortalizing functions of Epstein-Barr virus in human B lymphocytes. *Nature (London),* 340, 393–397.

Hammerschmidt, W. und Sugden, W. M. (1993) U.S. Pat. No. A-5 194 601.

Hammerschmidt, W. und Sugden, B. (1995) EP-A-0 694 613.

Hanahan, D. (1983) Studies on transformation of *Escherichia coli* with plasmids. *J. Mol. Biol.,* 166, 557–580.

Kempkes, B., Pich, D., Zeidler, R. und Hammerschmidt, W. (1995a) Immortalization of human primary B-lymphocytes in vitro with DNA. *Proc. Natl. Acad. Sci. USA,* 92, 5875–5879.

Kempkes, B., Pich, D., Zeidler, R., Sugden, B. und Hammerschmidt, W. (1995b) Immortalization of human B-lymphocytes by a plasmid containing 71 kpb of Epstein-Barr viral DNA. *J. Virol.,* 69, 231–238.

O'Connor, M., Peifer, M. und Bender, W. (1989) Construction of large DNA segments in *Escherichia coli. Science,* 244, 1307–1312.

Yates, J. L., Warren, N. und Sugden, B. (1985) Stable replication of plasmids derived from Epstein-Barr virus in various mammalian cells. *Nature (London),* 313, 812–815.

Firth, N., Ippen-Ihler, K., und Skurray, R. A. (1996): Structure and function of the F factor and mechanism of conjugation. In *Escherichia coli* and Salmonella, F. C. Neidhardt, R. Curtiss III, J. L. Ingraham, E. C. C. Iin, K. B. Low, B. Magasnik, W. S. Reznikoff, M. Riley, M. Schaechter and H. E. Umbarger, eds. (Washington, D.C.: American Society for Microbiology Press, 2377–2401).

Shizuya, H., Birren, B., Kim, U. J., Mancino, V., Slepak, T., Tachiiri, Y., und Simon, M. (1992): Cloning and stable maintenance of 300-kilobase-pair fragments of human DNA in *Escherichia coli* using an F-factor-based vector. *Proc. Natl. Acad. Sci. USA* 89, 8794–8797.

somal form or establishing a target cell that already naturally includes the DNA virus genome in an extrachromosomal form;

(b) introducing a DNA segment into the eukaryotic target cell at least comprising, operably linked to each other, a sequence controlling replication of the viral DNA genome in prokaryotic cells and at least one marker gene selectable in prokaryotic cells, and which is flanked by homologous DNA segments of the DNA virus genome having a length which enables recombination;

(c) integrating the DNA segment defined in (b) into the DNA virus genome by homologous recombination; optionally (d) selecting such target cells containing an extrachromosomal recombinant viral DNA genome; and (e) optionally purifying and isolating the recombinant DNA virus vector genome.

2. The method according to claim 1, wherein said genome of the DNA virus is a size of ≧120 kbp.

3. The method according to claim 2, wherein said genome of the DNA virus is ≧150 kbp.

4. The method according to claim 3, wherein said genome of the DNA virus is ≧170 kbp.

5. The method according to claim 1, wherein the DNA segment in step (b) further comprises a marker gene selectable in eukaryotic cells.

6. The method according to claim 1, wherein said flanking homologous DNA segments in step (b) are sequences having a size of ≧300 bp.

7. The method according to claim 6, wherein said flanking homologous DNA sequences have a size of ≧1 kbp.

8. The method according to claim 7, wherein said flanking homologous DNA sequences have a size of ≧2 kbp.

9. The method according to claim 1, further comprising the step of linearizing said DNA segment in step (b) prior to introduction.

TABLE 1

| EBV genome | F factor plasmid | EBV locus | EBV left coordinates | pMBO131 replicon | hygromycin phosphotransferase | EBNA2/ EBNA-LP | Green fluorescence protein | EBV right coordinates |
|---|---|---|---|---|---|---|---|---|
| 2010 | p1944.12 | deletion in B95.8 | #143,458–#52,636 (BsaBI/BsaBI) | yes | yes | no | yes | #149,930–#159,880 (ClaI/AscI) |
| 2087.2a | p2061.2 | terminal repeats (TR) in P3HR1/HH514 | #165,840–#169,924 (BstEII/BstEII) | yes | yes | no | no | #1–#3959 (EcoRI/BamHI) |
| 1947 (K clone) | p1820.15 | EBNA2 deletion in P3HR1/HH514 | #8994–#50,304 (EcoRI/PmeI) | yes | no | yes | no | #50,305–#56,083 (PmeI/SalI) |

Legend:
EBV locus indicates the genomic location into which the linearized F factor plasmids p1820.15, p1944.12 or p2061.2 were introduced by homologous recombination. As the EBV strains were used either the prototype strain B95.8 or the P3HR1/HH514 strain. The EBV regions flanking the linearized plasmids as homologous EBV genomic fragments are indicated by their EBV coordinates which refer to the prototype strain B95.8 and which are present in comparable form also in P3HR1/HH514. pMBO131 indicates the portion of the *E. coli* F factor plasmid. Hygromycin phosphotransferase and EBNA2/EBNA-LP refer to genes permitting the selection for homologous recombination events between the EBV strains (B95.8 or P3HR1/HH514) and the linearized F factor plasmids p1820.15, p1944.12 or p2061.2. Green fluorescence protein is a phenotypic marker gene.

What is claimed is:

1. A method for the preparation of DNA virus vectors capable of replication in eukaryotic as well as in prokaryotic cells, at least comprising the following steps of:

(a) introducing a DNA virus genome ≧100 kbp into a eukaryotic target cell and establishing such cells containing the viral DNA genome at least in extrachromo- 10. The method according to claim 1, wherein said DNA segment in step (b) comprises at least one segment of the *E. coli* plasmid F factor comprising the function for replication and a marker selectable in *E. coli*.

11. The method according to claim 1, wherein said DNA segment in step (b) further comprises at least one gene of interest to be expressed.

12. The method according to claim 1, wherein the homologous DNA segment in step (b) is selected so that by recombination a mutation is introduced into the viral genome.

13. The method according to claim 1, wherein the isolated recombinant DNA virus vector genome is introduced into a prokaryotic cell.

14. The method according to claim 13 wherein said prokaryotic cell is an *E. coli* cell.

15. The method according to claim 1, wherein the recombinant DNA virus vector genome is introduced into a eukaryotic cell for expression of foreign proteins from at least one gene of interest.

16. The method according to claim 1 further comprising the step (f) of introducing mutations into the resulting recombinant DNA virus vector genome.

17. The method according to claim 16 wherein the mutations are introduced by recombination with a vector capable of replication in the prokaryotic cell.

18. The method according to claim 16 wherein the step (f) of introducing mutations comprises an introduction of nucleotide additions.

19. The method according to claim 18 wherein the introduction of nucleotide additions comprises the introduction of at least one gene of interest to be expressed.

20. The method according to claim 1, wherein said step (a) of introducing the DNA virus genome or said step (b) of introducing the DNA segment is performed by infection, transfection or electroporation.

21. The method according to claim 1, wherein the sequence controlling replication and the at least one marker gene in step (b) comprise sequences which are in part homologous to each other and have a length rendering them capable for homologous recombination so that following homologous recombination the sequence controlling replication and the at least one marker gene are eliminated.

22. The method according to claim 1 further comprising the steps of:
(f) introducing said recombinant DNA virus vector genome of step (e) into a prokaryotic cell;
(g) introducing a plasmid into the prokaryotic cell comprising a stretch of DNA including at least, operably linked to each other, a DNA sequence which bears a mutation compared to the DNA segment introduced in step (b) and present on the DNA virus vector genome and a selectable marker gene, said stretch of DNA being flanked by DNA segments of a length sufficient to enable a recombination with the DNA virus vector genome;
(h) integrating the stretch of DNA described in (g) by recombination into the DNA virus genome;
(i) optionally purifying and isolating the recombinant DNA vector.

23. The method according to claim 22, wherein the plasmid in step (g) further comprises sequence motifs recognizable by a recombinase and prior to step (i) the selectable marker gene introduced by the recombination is removed by site-directed recombination via the sequence motifs recognized by the recombinase.

24. The method according to claim 1 wherein said viral genome comprises one or more cis-acting DNA segments.

25. The method according to claim 24, wherein a mutation is introduced on one or more of the cis-acting segments of the viral DNA genome which prevents the packaging of the viral DNA genome.

26. A method for making a DNA viral vector comprising the steps of:
(i) introducing a DNA virus genome into a eukaryotic target cell;
(ii) introducing a DNA segment into said eukaryotic target cell, said DNA segment comprising, operably linked to each other:
(A) a DNA segment controlling replication of the viral DNA genome in prokaryotic cells;
(B) at least one marker gene selectable in prokaryotic cells; wherein said DNA segment introduced into said eukaryotic target cell is flanked by homologous DNA segments of the DNA virus genome having a length which enables recombination;
(iii) integrating the segment introduced in step (ii) into the DNA virus genome by recombination.

27. The method according to claim 26, further comprising the step of:
(iv) selecting target cells comprising an extrachromosomal recombinant viral DNA genome.

28. The method according to claim 27, further comprising the step of:
(v) purifying and isolating the recombinant DNA virus vector genome.

29. The method according to claim 26, wherein the DNA virus genome is $\geq 100$ kbp.

* * * * *

UNITED STATES PATENT AND TRADEMARK OFFICE
CERTIFICATE OF CORRECTION

PATENT NO.     : 6,291,246 B1
DATED          : September 18, 2001
INVENTOR(S)    : Henri-Jacques Delecluse et al.

It is certified that error appears in the above-identified patent and that said Letters Patent is hereby corrected as shown below:

<u>Title page,</u>
Item [75], correct spelling of name and address of inventors, replace as follows:
-- GSF-Forschungszentrum fuer Umwelt und Gesundheit GmbH
   Ingolstaedter Landstrasse 1
   D-85674 Oberschleissheim --

Signed and Sealed this

Twelfth Day of November, 2002

*Attest:*

*Attesting Officer*

JAMES E. ROGAN
*Director of the United States Patent and Trademark Office*